United States Patent [19]
Kuhlmann et al.

[11] Patent Number: 6,090,366
[45] Date of Patent: *Jul. 18, 2000

[54] PROCESS FOR THE PREPARATION OF AN ORGAN SPECIFIC ANTIBODIES LABELED WITH TECHNETIUM-99M

[75] Inventors: Ludwig Kuhlmann, Flörsheim am Main; Anton Mayer, Niedernhausen, both of Germany

[73] Assignee: CIS bio international, Gis sur Yvette Cedex, France

[*] Notice: This patent is subject to a terminal disclaimer.

[21] Appl. No.: 09/145,238

[22] Filed: Sep. 1, 1998

Related U.S. Application Data

[63] Continuation of application No. 08/468,355, Jun. 6, 1995, Pat. No. 5,863,517, which is a continuation of application No. 08/363,577, Dec. 22, 1994, abandoned, which is a continuation of application No. 08/217,764, Mar. 25, 1994, abandoned, which is a continuation of application No. 08/035,521, Mar. 12, 1993, abandoned, which is a continuation of application No. 07/829,261, Feb. 3, 1992, abandoned.

[30] Foreign Application Priority Data

Feb. 5, 1991 [DE] Germany ............... 41 03 370

[51] Int. Cl.⁷ ............... A61K 51/10; C07F 5/00
[52] U.S. Cl. ............... 424/1.49; 424/1.69; 534/14
[58] Field of Search ............... 424/1.65, 1.69, 424/1.49, 1.41, 1.53, 1.73; 534/10, 14; 530/391.3, 391.5

[56] References Cited

U.S. PATENT DOCUMENTS

| | | | |
|---|---|---|---|
| 3,987,157 | 10/1976 | Molinski et al. | 424/1.37 |
| 5,116,596 | 5/1992 | Bremer et al. | 424/1.53 |
| 5,164,175 | 11/1992 | Bremer et al. | 530/391.3 |
| 5,175,343 | 12/1992 | Fritzberg et al. | 560/145 |
| 5,723,102 | 3/1998 | Bremer et al. | 424/1.69 |

FOREIGN PATENT DOCUMENTS

0271806  6/1988  European Pat. Off. ....... A61K 49/02

*Primary Examiner*—Jose' G. Dees
*Assistant Examiner*—Michael G. Hartley

[57] ABSTRACT

A process for the preparation of an organ-specific substance labeled with technetium-99m The invention relates to a process for the preparation of an organ-specific substance labeled with technetium-99m, in which no unwanted Tc-99m compounds are bound to the antibody. This is achieved by using the complexing agent required for the reducing agent in an amount which is stoichiometric relative to the reducing agent.

10 Claims, No Drawings

PROCESS FOR THE PREPARATION OF AN ORGAN SPECIFIC ANTIBODIES LABELED WITH TECHNETIUM-99M

This application is a Continuation of application Ser. No. 08/468,355, filed on Jun. 6, 1995, now U.S. Pat. No. 5,863,517, which is a continuation of application Ser. No. 08/363,577 filed Dec. 22, 1994, now abandoned, which is a continuation of application Ser. No. 08/217,764 filed Mar. 25, 1994, now abandoned, which is a continuation of application Ser. No. 08/035,521 filed Mar. 12, 1993, now abandoned, which is a continuation of application Ser. No. 07/829,261 filed Feb. 3, 1992, now abandoned.

DESCRIPTION

A process for the preparation of an organ-specific antibodies labeled with technetium-99m.

The invention relates to a process for the preparation of an organ-specific substance which is labeled with technetium-99m and which has been pretreated or coupled to a complexing agent for technetium-99m, where the organ-specific substance is mixed with pertechnetate-99m and a complex-stabilized reducing agent.

Proteins have been used successfully for many years in medical diagnosis with radioactive nuclides. Thus, for example, investigations on the heart can be carried out with human serum albumin (HSA) labeled with technetium-99m or other suitable nuclides.

Recently, immunoglobulins have become of prime importance, and monoclonal antibodies in particular are employed for diagnosing malignant lesions. Monoclonal antibodies have also proven useful in other areas of nuclear medicine diagnosis, for example in the location of foci of inflammation.

Initially, the antibodies were labeled with various iodine isotopes (iodine-123 or iodine-131) or indium-111. However, clinical trials showed that the use of the nuclide technetium-99m (Tc-99m), which has a very much shorter life, is likewise possible. This nuclide occupies an outstanding position in nuclear medicine because it has very favorable nuclear physical properties. In addition, the Mo-99/Tc-99m generator makes it available virtually at any time and at any location.

This is why a number of processes in which proteins are labeled with technetium-99m have been described. These can be divided into two large groups.

To be assigned to one group are all the processes which initially couple complexing agents of a wide variety of types to the antibody and, via these, stably bind the technetium-99m. However, this method has the disadvantage that the labeling yields are inadequately high and therefore purification steps are necessary for preparing the product ready for administration.

The method in which the technetium-99m is directly bound to the antibody belongs in the second group. Reactive groups are generated in the antibody for this purpose. These are generally SH groups which are generated by reduction of disulfide bridges with suitable reducing agents (for example 2-mercaptoethanol, 3-mercapto-1,2-propanediol, cysteine etc.). Proteins labeled in this way can be injected directly without special purification steps. The following processes from this group should be specifically picked out.

B. A. Rhodes describes the labeling of an anti-hCG antibody with Tc-99m (U.S. Pat. No. 4,472,371). The antibody is in this case treated with an excess of tin(II) ions which remains in the product. Tin(II) ions bring about the reduction of disulfide bridges to SR groups in the antibody and, on the other hand, also the reduction of pertechnetate-99m to Tc(IV)-99m. Tc-99m in this form is able to be bound to the antibody. Because of the large except of Sn(II) ions, not only does Tc-99m occur bound to the antibody but there is also formation of Tc compounds which must be removed (cf. U.S. Pat. No. 4,472,371: Example II). However, this is a serious disadvantage in terms of the conditions which must be maintained in the laboratory.

EP-A-0,271,806 describes a labeling method in which tin(II) ions are stored in complexed form separate from the antibody. Only shortly before the labeling are the two components mixed. The labeling unit therefore comprises two bottles. This is a disadvantage for the user because he has to manipulate two bottles which must not be mixed up.

The complex-stabilized Sn(II) ions are used as reducing agent in this case too. The complexing agent is employed in excess relative to Sn(II) ions, i.e. there is formation of complexes not only with Sn(II) ions but also with Tc-99m.

In other prior art publications, the Tc-99m complexes which are formed (with the complexing agent of Sn(II)) are deliberately generated in order to transfer Tc-99m to the antibody by means of the complex which is formed. The process is called transcomplexation:

According to EP-A-0,237,150, a Tc-99m tartrate or glucoheptonate is employed to label an antibody with Tc-99m.

Tc-99m complexes with sucrose, glucoheptonate, tartrate and arabonate are used in WO 88/07382 for the same purpose. Particular importance is in fact attached to the stability of these complexes.

Tc-99m tartrate is used for transcomplexation in WO 89/07456 too. A process is described therein in which the antibody is initially bound to a complexing agent.

The said processes in which Tc-99m is transferred to the antibody by transcomplexation have the disadvantage, due to the system, that the finished product contains unwanted Tc-99m compounds as a consequence of an uncontrollable reaction.

It was therefore an object of the present invention to provide a process for the preparation of an organ-specific substance labeled with technetium-99m, in which no unwanted Tc-99m compounds are bound to the antibody.

The object has been achieved by providing a process of the type described in the introduction, which comprises using the complexing agent which is required for the reducing agent in an amount which is stoichiometric relative to the reducing agent.

It has been surprisingly found—in contrast to previous ideas—that the process of transcomplexation is not necessary for transferring Tc-99m to the antibody.

It was completely surprising to realize that the complexing agent merely has the task of keeping Sn(II) ions in solution in a complex, i.e. preventing precipitation as Sn(II) hydroxide. The excess, hitherto used, of complexing agent which initiates the transcomplexation is unnecessary and, in the final analysis, also has considerable disadvantages: inter alia it has been necessary to store Sn(II) ions and antibody in two different vessels.

By contrast, the process according to the invention makes it possible for Sn(II) complex and antibody to be stored in one vessel.

Dithionite or Sn(II) ions are preferably used as reducing agent.

By the "stoichiometric" amount of complexing agent is meant the amount which is necessary to saturate completely the valencies of the Sn(II) ions and, at the same time, however also to achieve a complex of defined composition.

Stoichiometric Sn(II) complexes ought to be stable in a pH range from 3 to 11, preferably 4 to 7.

A general statement of the particular stoichiometric ratio of Sn(II) ions to the complexing agent cannot be given because this depends on the complexing agent chosen in each case.

Anionic complexes are particularly preferred. Among these in turn those with a 4-fold to a 8-fold negative charge. Charge equalization is ensured by alkali metal, alkaline earth metal or $NH_4^+$ ions.

The complexes of the Sn(II) ion with citric acid are very particularly preferred. The stoichiometric anionic Sn(II)-citric acid complex $[Sn(citrate)_2]^{4-}$ which forms is known (Gmelin, Handbuch der Anorganischen Chemie, Zinn (Handbook of Inorganic Chemistry, Tin) part C, pages 217–229, Heidelberg 1975).

By contrast, the complex, which is likewise particularly preferred, of the Sn(II) ion with 1,1,3,3-propanetetraphosphonic acid has not hitherto been described. However, it can be obtained by methods known to the person skilled in the art, in which 1,1,3,3-propanetetraphosphonic acid is reacted with Sn(II) in the molar ratio of 2:1 to one another, and forms a complex whose composition corresponds to this molar ratio (see below). By contrast, a molar ratio below that mentioned would lead to the formation of a sparingly soluble compound in which one molecule of phosphonic acid binds 4 Sn(II) ions.

Organ-specific substances according to the process according to the invention are in general carrier substances which have in their molecule at least one functional group with complexing properties. These groups are usually atoms or ions which act to donate an electron pair (Lewis bases). One such functional group with complexing property is, for example, an —SCN, —$NH_2$, —NHR, —$NR_2$, —COO, —OH, =S, —SH, —NO group.

Examples of representatives of such substances with functional complexing groups which may be mentioned are:

proteins (—NH, —$NH_2$ or COO groups), enzymes (—$NH_2$, —OH, —P=O groups), sugars (—OH groups) or polymers which have side chains with appropriate functional groups.

If the compound to be labeled does not have such a functional group, the substance must, before the labeling, be "pretreated" or coupled to a suitable complexing agent.

By "pretreated" are meant within the scope of the invention those measures which lead to the production of a functional group with complex-forming properties in the molecule to be labeled. For example, antibodies contain disulfide bridges. However, the two sulfur atoms which are covalently linked to one another are not in this form able to complex technetium-99m. However, reduction of the disulfide bridge produces two SH groups which now themselves represent excellent complexing ligands for technetium-99m and, moreover, bind the latter in good yields.

Another possibility for binding technetium-99m to organ-specific substances which do not have a functional group with complexing properties comprises incorporating such a functional group into the molecule or chemically bonding a complexing agent to the molecule.

The process appears particularly interesting for the technetium-99m labeling of antibodies. Partial reduction of the S—S bonds of the antibody or of an $F(ab')_2$ antibody fragment can be achieved at room temperature by brief exposure to mild reducing agents (pretreatment of the organ-specific substance). Particularly suitable reducing agents are monothiols such as 2-mercaptoethanol or 2-mercaptoethylamine (cysteamine). Obtained in this case are reactive antibody molecules which have neither lost their immunological reactivity nor been fragmented to smaller fragments. Suitable in principle for the partial reduction of the antibody or the $F(ab')_2$ antibody fragment are all reducing agents which cleave only some of the S—S bonds even on a lengthy exposure time and do not lead to any fragmentation of the antibody component. The time the antibody component is exposed to a reducing agent of this type does not need to exceed one hour. In general, after only 10 to 30 minutes sufficient SH groups have been produced for adequate amounts of technetium-99m cations to be bound. The excess reducing agent is then removed and the partially reduced antibody is isolated in a buffered solution (for example 0.02 M phosphate solution, pH 7.2) and lyophilized without delay. It is necessary to suppress reoxidation of the free thiol groups in the antibody by atmospheric oxygen during this. The lyophilized antibody which, apart from the buffer substances, contains no further additives and is blanketed with nitrogen as protective gas can be stored at refrigerator temperature (−5 to +5° C.) for weeks without alteration; it redissolves satisfactorily on addition of isotonic sodium chloride solution.

The partially reduced antibody component prepared in this way (pretreated organ-specific substance) can now be labeled smoothly with Tc-99m by the process according to the invention when a mixture of pertechnetate and stoichiometric Sn(II) complex is added to it.

The procedure for the preparation of a diagnostic aid ready for use can now be such that first the lyophilized antibody component is dissolved in a technetium-99m-pertechnetate solution and then the reduction and binding of the technetium to the antibody is brought about by adding a solution of the tin(II) complex.

However, the diagnostic aid can also be prepared by first dissolving the antibody component in the tin(II) complex-containing solution and subsequently labeling the lyophilized antibody component with technetium by addition of technetium-99m-pertechnetate solution.

To prepare a diagnostic aid which contains a technetium-99m-labeled organ-specific substance it is expedient to put together an assay which contains the organ-specific substance or the pretreated organ-specific substance or the organ-specific substance coupled to a complexing agent for Tc-99m, where appropriate mixed with a buffer, and the complex-stabilized tin(II) salt which is required to reduce the technetium on the organ-specific substance. An assay in which the lyophilized, where appropriate pretreated, organ-specific substance is mixed with disodium hydrogen phosphate (pH 7.2) as buffer substance has proven particularly useful. In this way, after a short reaction time, for example after only 5 minutes, there is obtained virtually quantitative technetium-99m-labeling of the substance, which contains less than 1% free pertechnetate and only very small amounts of Tc-99m-labeled tin(II) component as impurities, so that subsequent purification processes are no longer necessary.

The organ-specific substance prepared by the process according to the invention ensures—although it is stored in one vessel with the Sn(II) complex—unaltered stability of the lyophilized product. This ensures rapid, straightforward and satisfactory labeling of the organspecific substance.

The stabilizer present in some labeling kits is also advantageous in antibody labeling because it guarantees an even longer stability of the injection solution.

The examples which follow are intended to illustrate the invention:

EXAMPLE 1

Preparation of a Stable Complex Between Tin(II) and 1,1,3,3-Propanetetraphosphonic Acid 0.5240 g (1.0 mmol) of tetrasodium 1,1,3,3-propanetetraphosphonate tetrahydrate (PTP) is dissolved in 100 ml of water. 0.2257 g (1.0 mmol) of tin(II) dichloride dihydrate is dissolved in 100 ml of 0.1 N hydrochloric acid. In a beaker, 2 ml (0.02 mmol) of the PTP solution in 1 ml (0.01 mmol) of the tin(II) solution are mixed together and the pH is adjusted to a required value between pH=3 to 11 with 2 N sodium hydroxide solution. A clear solution is obtained.

Mixing of 1 ml (0.01 mmol) of the PTP solution and 1 ml (0.01 mmol) of the tin(II) solution immediately results in a precipitate which cannot be dissolved even by changing the pH in the range from pH=3 to 11. Detectable in the supernatant are no tin(II) ions but still 3 equivalents of PTP.

The preparation of the tin(II) citrate complex is described in Example 2.

EXAMPLE 2

Preparation of a Tin(II) Complex With Citric Acid 0.12955 g of anhydrous citric acid and 0.07603 g of tin(II) dichloride dehydrate are dissolved in 10 ml of water. The solution is diluted to 900 ml with water, the pH is adjusted to pH=6.5 to 7 with 2 N sodium hydroxide solution and then the volume is made up to exactly 1 l with water. The solution contains 40 Ag of SN(II) per ml and can be used directly for the preparation of the antibody products.

The following example shows the preparation of a labeling kit with the monoclonal antibody BW 494/32. This antibody reacts with antigens which are expressed mainly by mammary or ovarian carcinoma cells.

EXAMPLE 3

Preparation of a Labeling Unit With the Monoclonal Antibody BW 494/32

0.5 ml of the solution from Example 1 or Example 2 is added to 1 ml of a solution of the antibody, containing 1 mg of immunoglobulin, which has been treated with 2-mercaptoethanol, 3-mercapto-1,2-propanediol or with another suittogetheducing agent. The solutions are mixed together and then freeze-dried.

The procedure for labeling with Tc-99m is as follows.

The eluate from a commercially available generator with an activity of 500 MBq to 1500 MBq is added to the lyophilizate. This activity can be present in a volume of 1 ml to 10 ml. The product is ready for injection after a time of 5 min to 10 min has elapsed.

Examination of the radiochemical purity by thin-layer chromatography (ITLC SG/methyl ethyl ketone) or high performance liquid chromatography (gel filtration column (for example Bio Rad TSK 250), 0.1 M phosphate buffer pH 6.8, flow rate: 1 ml/min) showed that between 95% and 99% of the added activity was bound to the antibody. This solution remained sufficiently stable until a time of up to 24 hours had elapsed.

In an animal experiment on nude mice with tumors, storage levels in the tumor between 6 and 7%/g of tumor were achieved with these products.

What is claimed is:

1. A process for preparing of an organ-specific antibody or antibody F(ab')$_2$ fragment directly labeled with technetium-99m, comprising:
   (a) pretreating an organ-specific antibody or antibody F(ab')$_2$ fragment to produce a functional group having complex-forming ability on the antibody or antibody F(ab')$_2$ fragment,
   (b) combining a complexing agent with a reducing agent, wherein the complexing agent and reducing agent are present in stoichiometric quantities to produce a complex-stabilized reducing agent, and
   (c) mixing the pretreated antibody or antibody F(ab')$_2$ fragment from (a) with pertechnetate-99 m and the complex stabilized-reducing agent from (b).

2. The process of claim 1, wherein the complex-stabilized reducing agent is stable in the pH range from 3 to 11.

3. The process of claim 1, wherein the complexing agent is anionic.

4. The process of claim 1, wherein the reducing agent is Sn(II) ions.

5. The process of claim 1, wherein an organ-specific antibody is prepared.

6. The process of claim 1, wherein an organ-specific antibody F(ab')$_2$ fragment is prepared.

7. The process of claim 1, wherein the antibody or antibody F(ab')$_2$ fragment binds to a tumor-specific antigen.

8. The process of claim 1, wherein the antibody is a monoclonal antibody.

9. The process of claim 1, wherein the complexing agent is citrate or an anion of 1,1,3,3-propanetetraphosphonic acid.

10. The process of claim 1, wherein (a) comprises partially reducing disulfide bonds present in the antibody or antibody F(ab')$_2$ fragment.

* * * * *

UNITED STATES PATENT AND TRADEMARK OFFICE
CERTIFICATE OF CORRECTION

PATENT NO. : 6,090,366
DATED : July 18, 2000
INVENTOR(S): Ludwig KUHLMANN, et al.

It is certified that an error appears in the above-identified patent and that said Letters Patent is hereby corrected as shown below:

On the Title Page, Item [54] and Column 1, the Title should read as follows:

[54] PROCESS FOR THE PREPARATION OF AN ORGAN-SPECIFIC SUBSTANCE LABELED WITH TECHNETIUM-99M

On the Title Page, Item [73] the Assignee should read as follows:

[73] Assignee: CIS bio international, Gif sur Yvette Cedex, France

Signed and Sealed this

Seventeenth Day of April, 2001

Attest:

NICHOLAS P. GODICI

*Attesting Officer*  *Acting Director of the United States Patent and Trademark Office*